United States Patent
Kumar et al.

(10) Patent No.: US 10,098,813 B2
(45) Date of Patent: Oct. 16, 2018

(54) PERFUSION DOSAGE FORM (71) Applicant: SUN PHARMACEUTICAL INDUSTRIES LIMITED, Mumbai (IN)

(72) Inventors: Samarth Kumar, Baroda (IN); Prashant Kane, Baroda (IN); Balaram Subhas Bhowmick, Baroda (IN); Kirti Ganorkar, Baroda (IN); Nishit Patel, Baroda (IN); Anilrao Ashish Dubewar, Baroda (IN); Mukeshbhai Umeshkumar Patel, Baroda (IN)

(73) Assignee: SUN PHARMACEUTICAL INDUSTRIES LIMITED, Mumbai (IN)

(*) Notice: Subject to any disclaimer, the term of this patent is extended or adjusted under 35 U.S.C. 154(b) by 408 days.

(21) Appl. No.: 14/843,296

(22) Filed: Sep. 2, 2015

(65) Prior Publication Data
US 2016/0058663 A1    Mar. 3, 2016

(30) Foreign Application Priority Data
Sep. 3, 2014  (IN) .................. 2804/MUM/2014

(51) Int. Cl.
    A61J 1/10    (2006.01)
    G06F 19/00   (2018.01)
    (Continued)

(52) U.S. Cl.
    CPC . A61J 1/10 (2013.01); A61J 1/16 (2013.01); A61M 5/14 (2013.01); A61M 5/1408 (2013.01);
    (Continued)

(58) Field of Classification Search
    CPC ..... A61J 1/10; A61J 1/16; A61M 5/14; B65D 81/266; B65B 55/04
    See application file for complete search history.

(56) References Cited

U.S. PATENT DOCUMENTS

| 5,786,344 A | 7/1998 | Ratain et al. |
| 6,403,569 B1 | 6/2002 | Achterrath |
| (Continued) | | |

FOREIGN PATENT DOCUMENTS

| WO | 2009111294 A1 | 9/2009 |
| WO | 2015006822 A1 | 1/2015 |

OTHER PUBLICATIONS

Van Riel, Jmgh et al., "Continuous infusion of hepatic arterial irinotecan in pretreated patients with colorectal cancer metastatic to the liver," Ann Oncol., 15:59-63 (2004).

(Continued)

Primary Examiner — Leslie Deak
(74) Attorney, Agent, or Firm — Sughrue Mion, PLLC (57) ABSTRACT The present invention relates to a method for enabling hospitals or clinics to administer a dose of a drug to patients in need thereof while avoiding steps of manipulation, dilution, reconstitution, dispensing, sterilization, transfer, handling or compounding before intravenous administration.
The present invention further relates to a perfusion system comprising different sets of perfusion containers, each container comprising a ready-to-infuse, stable, sterile, aqueous perfusion solution of a drug, wherein the set of perfusion containers alone or in combination provides for direct intravenous administration of a desired dose of the drug to a patient in need thereof, such that the delivered dose is equal to or within ±5% of the calculated dose.

1 Claim, 1 Drawing Sheet (51) Int. Cl.
  *B65B 55/04* (2006.01)
  *B65D 81/26* (2006.01)
  *A61M 5/14* (2006.01)
  *A61J 1/16* (2006.01)
(52) U.S. Cl.
  CPC ............ *B65B 55/04* (2013.01); *B65D 81/266* (2013.01); *G06F 19/3456* (2013.01)

(56) References Cited

U.S. PATENT DOCUMENTS

| | | | |
|---|---|---|---|
| 6,673,805 B2 * | 1/2004 | Lauria | A61K 9/0019 514/283 |
| 6,794,370 B2 | 9/2004 | Achterrath | |
| 7,235,583 B1 | 6/2007 | Webb et al. | |
| 7,479,499 B2 | 1/2009 | Govindarajan et al. | |
| 7,490,639 B2 | 2/2009 | Py | |
| 7,992,597 B2 | 8/2011 | Py et al. | |
| 2008/0242691 A1 | 10/2008 | Nakazawa et al. | |
| 2009/0221622 A1 | 9/2009 | Teja et al. | |
| 2010/0111941 A1 | 5/2010 | Deitcher et al. | |
| 2011/0177161 A1 | 7/2011 | Nekkanti et al. | |
| 2012/0323212 A1 | 12/2012 | Murphy et al. | |
| 2013/0333796 A1 | 12/2013 | Py | |
| 2014/0005135 A1 | 1/2014 | Prestrelski et al. | |
| 2014/0005603 A1 | 1/2014 | Holtwick et al. | |
| 2015/0045289 A1 * | 2/2015 | West | A61J 1/10 514/2.9 |

OTHER PUBLICATIONS

Dodds, H.M., et al., "Photodegradation of irinotecan (CPT-11) in aqueous solutions; identification of fluorescent products and influence of solution composition," *J Pharm Sci.*, 86(12):1410-6 (1997).

Thiesen J., et al., "Physicochemical stability of irinotecan injection concentrate and diluted infusion solutions in PVC bags," *J Oncol Phar Pract.*, vol. 6 (3):115-121 (2000).

Li W. Y. et al, "Stability of irinotecan hyrochloride in aqueous solutions," *Am J. Health Syst Pharm.*, vol. 59, pp. 539-544 (2002).

* cited by examiner

PERFUSION DOSAGE FORM

FIELD OF THE INVENTION

The present invention relates to a method for enabling hospitals or clinics to administer a dose of a drug to patients in need thereof while avoiding steps of manipulation, dilution, reconstitution, dispensing, sterilization, transfer, handling or compounding before intravenous administration.

The present invention further relates to a perfusion system comprising different sets of perfusion containers, each container comprising a ready-to-infuse, stable, sterile, aqueous perfusion solution of a drug, wherein the set of perfusion containers alone or in combination provides for direct intravenous administration of a desired dose of the drug to a patient in need thereof, such that the delivered dose is equal to or within ±5% of the calculated dose.

BACKGROUND OF THE INVENTION

There are drawbacks associated with most of the commercially available parenteral dosage forms, particularly parenteral dosage forms of chemotherapeutic agents.
1. First, these marketed products cannot be directly administered to a patient & rather require manipulation, the concentrated solution needs to be diluted or the lyophilized powder needs to be reconstituted using a suitable solvent, prior to infusion.
2. Second, besides the inconvenience, the manipulation exposes the involved personnel (workers, pharmacists, medical personnel, nurses) to risk of exposure to the cytotoxic drugs.
3. Any manipulation may compromise the sterility required in intravenous perfusions, particularly when they are designed to be preservative free.
4. On preparation of this solution for intravenous infusion, ideal optimum conditions such as the desired pH at which drug is most stable, are disturbed. Therefore, if the infusion is stored, the degradation occurs more rapidly.
5. Human manipulation is associated with medication/dosing errors. Antineoplastic drugs, in particular have a low therapeutic index. Medication errors in dosing or dosing rate can have highly undesirable consequences and result in an unfavorable therapeutic outcome.

The present invention provides a method which enables accurate dosing of the drug to the patients while avoiding the above mentioned errors. The method of the present invention avoids steps of manipulation, dilution, reconstitution, dispensing, sterilization, transfer, handling or compounding before intravenous administration of desired dose of drug.

SUMMARY OF THE INVENTION

The present invention provides a method for enabling hospitals or clinics to administer a dose of a drug to patients in need thereof while avoiding steps of manipulation, dilution, reconstitution, dispensing, sterilization, transfer, handling or compounding before intravenous administration, the method comprising:
(a) manufacturing a first set of perfusion containers containing a ready-to-infuse, stable, sterile, aqueous perfusion solution of the drug at a first higher concentration, and a second set of top-up perfusion containers containing a ready-to-infuse, stable, sterile, aqueous perfusion solution of the drug at a second concentration and optionally a third set of top-up perfusion containers having a ready-to-infuse, stable, sterile, aqueous perfusion solution of the drug at a third concentration, the first concentration of drug being higher than the second and third concentrations, the containers within each set of perfusion containers ranging in volume from a lower to a higher volume,
(b) calculating the dose to be administered to patients according to at least one patient parameter and providing instructions for selecting one or more perfusion container(s) from the first set and if required one or more top-up perfusion container(s) from the second or third set and for directly administering the drug from the selected perfusion containers such that the delivered dose is equal to or within ±5% of the calculated dose,
(c) supplying to the distributors or hospitals or clinics, the first set of perfusion containers and second or third set of top-up containers along with the instructions.

According to a further aspect of the present invention, there is provided a perfusion system comprising:
a first set of perfusion containers comprising a ready-to-infuse, stable, sterile, aqueous perfusion solution of a drug at a first higher concentration, and a second set of top-up perfusion containers comprising a ready-to-infuse, stable, sterile, aqueous perfusion solution of the drug at a second concentration and optionally a third set of top-up perfusion containers comprising a ready-to-infuse, stable, sterile, aqueous perfusion solution of the drug at a third concentration, the first concentration of drug being higher than the second and third concentrations, the first to the third sets of perfusion containers ranging in volume from a higher volume to a lower volume,
instructions for selecting one or more perfusion container(s) from the first set and if required one or more top-up perfusion container(s) from the second or third set and for directly administering the drug from the selected perfusion containers such that the delivered dose is equal to or within ±5% of a dose calculated according to at least one patient parameter,
wherein the set of perfusion containers alone or in combination provides for direct intravenous administration of a desired dose of the drug to a patient in need thereof, such that the delivered dose is equal to or within ±5% of the calculated dose.

DETAILED DESCRIPTION OF THE PRESENT INVENTION

The term "perfusion" as used herein in the present invention, refers to the passage of fluid through the lymphatic system or blood vessels to an organ or tissue, in particular this term refers to the slow or prolonged intravenous infusion or administration of a solution of active ingredient to a patient.

The term "ready-to-infuse' or 'directly administering' or 'direct intravenous infusion' or 'direct delivery' as used herein refers to direct intravenous infusion of the aqueous drug solution to the patient without involving any intermediate steps of manipulation, dilution, reconstitution, dispensing, sterilization, transfer, handling or compounding before intravenous parenteral administration of the drug solution. The aqueous drug solution can be directly administered parenterally from the perfusion container.

The term 'calculated dose' as used herein means the dose of the drug that is to be administered to the patient depending upon the disease condition or in other terms indication and the patient parameters such as body surface area, body weight, renal clearance or hepatic function and other factors, that may affect the dose calculation.

The term 'delivered dose' as used herein means the dose of the drug that is delivered to the patient from the perfusion container of the first set and optionally the perfusion container from the second and the third set. The delivered dose according to the method of the present invention is equal to or within ±5% of the calculated dose. The % variation may be calculated as the % of difference between the delivered dose and the calculated dose, divided by the calculated dose.

The term 'top-up perfusion containers' refer to the perfusion containers containing the aqueous solution of the drug at a concentration lower than the concentration of the aqueous solution of the drug present in the primary or the first set of the containers.

The term "sterile" or 'sterilized' as used in the context of the invention, means a solution that has been brought to a state of sterility and has not been subsequently exposed to microbiological contamination, i.e. the sterility of the aqueous solution present in the perfusion container has not been compromised.

The term 'stable' as used herein means that the aqueous perfusion solution filled in the container is physically as well as chemically stable as demonstrated by compliance to acceptable specification, when the dosage form is stored at room temperature (about 25° C. and 40% relative humidity) for twelve months, preferably eighteen months, more preferably 24 months or longer.

According to the method or system of the present invention, there is provided a first set of perfusion containers containing a ready-to-infuse, stable, sterile, aqueous perfusion solution of the drug at a first higher concentration. This solution is generally administered at a higher concentration and in higher volumes than solutions of the drug from the other set(s) of perfusion containers. The second or the third sets of perfusion containers include the aqueous perfusion solution of the drug at a concentration lower than the first concentration of drug (as provided in the first set of perfusion containers). The first to third sets of perfusion containers range in volume from a higher to a lower volume. The sets of sterile perfusion containers filled with sterile aqueous solutions of drug are particularly, manufactured in a pharmaceutical manufacturing site and not in hospital premises where there may be intermediate steps of dispensing or mixing of the aqueous solution which has been manufactured separately in a manufacturing plant or site and supplied in bulk volumes to the hospital or pharmacy. The perfusion containers are filled with the aqueous perfusion solution of the drug and the perfusion containers are subjected to sterilization process in the pharmaceutical manufacturing facility.

Generally the volume of a container from the first set of containers is greater than the volume of a container from the second and third sets of containers, and the volume of a container from the second set of containers is generally greater than the volume of a container from the third set of containers.

According to an embodiment of the invention, the volume of a container from the first set of containers is greater than the volume of a container from the second and third sets of containers, and the volume of a container from the third set of containers is around the same as the volume of a container from the second set of containers. Each container in a set of containers may have the same volume or a different volume. Generally each container in a set has a different volume. According to one embodiment, the second and optionally the third set of containers have an associated volume of 10% to 90% of the volume of a container of the first set of containers having the lowest associated volume; generally 50% to 75%.

Generally the concentration of the solution of the drug in the first set of containers is greater than the concentration of the solution of the drug in the second and third sets of containers. The concentration of the solution of the drug in the second set of containers may be greater than or the same as the concentration of the drug in the third set of containers. According to one embodiment, the concentration of the solution of the drug in the second and optionally the third set of containers is 10% to 95% less than the concentration of the solution of the drug in the first set of containers; generally 75% to 95% less. Typically, the concentration of the solution of the drug in the second set of containers is 10% to 30% of the concentration of the solution of the drug in the first set of containers. Typically, the concentration of the solution of the drug in the third set of containers is 5% to 15% of the concentration of the solution of the drug in the first set of containers.

A dose to be administered to patients may be calculated according to at least one patient parameter. Instructions, in particular written instructions are provided for selecting one or more perfusion container(s) from the first set and if required one or more top-up perfusion container(s) from the second or third set and for directly administering the drug from the selected perfusion containers such that the delivered dose is equal to or within ±5% of the calculated dose. Suitably, the patient parameter according to which the dose to be administered to the patient is calculated may be selected from the group consisting of one of patient's body surface area, body weight or ideal body weight, hepatic function or renal function. In some preferred embodiments, the patient parameter is patient's body surface area.

Further, the present invention may include supplying to the distributors or hospitals or clinics the first set of perfusion containers and second or third set of top-up containers along with the instructions, generally in the form of written instructions.

The method or system of the present invention avoids steps of manipulation, dilution, reconstitution, dispensing, sterilization, transfer, handling or compounding before intravenous administration of desired dose of drug. Suitably, the method avoids any manipulation, any step of reconstituting or dilution such as those involved in conventional lyophilized or concentrated products. The method further does not involve any step of transfer of infusion solution from one container to another before administration or any volume adjustment, i.e. addition or withdrawal of the aqueous solution from the perfusion container, before administration. The method of the present invention thus eliminates the risk of any potential calculation or dilution error as well as risk of microbiological contamination prior to administration. The method of the present invention also eliminates or minimizes contact of the drugs by hospital personnel, thus avoiding any potential side effects associated with the drug, especially with cytotoxic anti-cancer drugs.

The drug according to the method or system of the present invention is an active ingredient selected from the group consisting of anti-cancer/chemotherapeutic agents, antibiotics or antibacterial agents, analgesic or anaesthetic agents, alpha adrenergic agonists, beta-adrenergic agonists, muscle relaxants, antifungal agents, antiviral agents. Suitably, the drug may be selected from the group consisting of anti-cancer drugs/chemotherapeutic agents such as, but not limited to irinotecan, topotecan, pemetrexed, docetaxel, paclitaxel, gemcitabine, cisplatin, oxaliplatin, carboplatin, leukovorin, etoposide, doxorubicin, daunonibicin, epirubicin, idarubicin, vincristine, vinblastine, vinorelbine, 5-flourouracil, ifosfamide, cyclophosphamide, mechlorethamine, carmustine, dacarbazine, cladribine, fulvestrant, pegfilgrastim, pamidronate, zoledronic acid, mitoxantrone, streptozocin, mitomycin, gentamicin, teniposide; Antimicrobial agents such as, but not limited to vancomycin, methicillin, daptomycin, tobramycin, amikacin, ticarcillin; Analgesics or anesthetic agents such as, but not limited to midazolam, propofol, fentanyl, remifentanil, thiopental; Muscle relaxants such as, but not limited to rocuronium, vecuronium, atracurium; Antifungal agents such as, but not limited to voriconazole, Antiviral agents such as, but not limited to acyclovir.

In preferred embodiments, the drug is selected from the group consisting of anticancer agents. In one preferred embodiment, the drug is irinotecan or its pharmaceutically acceptable salt. Preferably, the salt is hydrochloride salt. Irinotecan or its pharmaceutically acceptable salt, for example irinotecan hydrochloride may be used in the method of the present invention at a concentration ranging from about 0.1 mg/ml to about 3.0 mg/ml; preferably, from about 0.2 mg/ml to about 2.0 mg/ml.

Suitably, according to one preferred embodiment of the present invention, the first set of perfusion containers contains a ready-to-infuse, stable, sterile, aqueous perfusion solution of drug, irinotecan hydrochloride, at a first higher concentration, which first higher concentration may range from about 1.0 mg/ml to about 3.0 mg/ml. Preferably, the first higher concentration is 1.5 mg/ml. According to this embodiment, the second or third set of infusion container contain a ready-to-infuse, stable, sterile, aqueous perfusion solution of irinotecan hydrochloride at a concentration ranging from about 0.1 mg/ml to 0.8 mg/ml, preferably from about 0.1 mg/ml to 0.6 mg/ml. Preferably, the second and third set of infusion containers contain the ready-to-infuse, stable, sterile, aqueous perfusion solution of irinotecan hydrochloride, at a concentration of 0.4 mg/ml and 0.2 mg/ml respectively.

Preferably, the set of perfusion containers according to the present invention may range in volume from a lower to a higher concentration. The volume of the aqueous solution filled in the first set of perfusion containers may vary from about 50 ml to about 1000 ml, preferably from about 60 ml to about 800 ml, more preferably from about 80 ml to about 500 ml. Suitably, the volume of the aqueous solution filled in the second and third set of perfusion containers may vary from about 10 ml to about 100 ml, preferably from about 25 ml to about 80 ml, more preferably from about 40 to 60 ml.

In one preferred embodiment, wherein the drug is irinotecan or its pharmaceutically acceptable salt, the volume of the aqueous solution filled in the first set of perfusion containers may vary from about 50 ml to about 500 ml, preferably from about 80 ml to about 300 ml. In specific embodiments, the first set of container may incorporate 90 ml, 100 ml, 120 ml, 150 ml, 180 ml, 200 ml, 210 ml, 240 ml, 270 ml or 300 ml of the aqueous solution of irinotecan or its pharmaceutically acceptable salt. In this preferred embodiment, the volume of the aqueous solution filled in the second and third set of top-up perfusion containers may vary from about 10 ml to about 100 ml, preferably from about 25 ml to about 75 ml. In specific embodiments, the second and third set of top up perfusion containers may incorporate about 50 ml of the aqueous solution of irinotecan or its pharmaceutically acceptable salt. In one embodiment, the different set of perfusion containers having different volumes may be distinguished. In particular the different sets of perfusion containers may be visually distinguished, for example through the use of different patterns or colours on some or all of the containers. In particular different colours may be used for labeling.

In one preferred embodiment, the drug is irinotecan hydrochloride and the ready-to-infuse, stable, sterile, aqueous perfusion solution of irinotecan hydrochloride has a pH ranging from about 3.0 to 4.5, and irinotecan hydrochloride is present in the first set of infusion containers at concentration ranging from about 1.0 mg/ml to 3.0 mg/ml and in the second or third set of infusion containers at a concentration ranging from about 0.1 mg/ml to 0.6 mg/ml. In one preferred particularly embodiment irinotecan hydrochloride is present in the first set of infusion containers at a concentration of 1.5 mg/ml and at a volume ranging from about 50 ml to about 300 ml, in the second set of infusion containers at a concentration of 0.4 mg/ml and at a volume ranging from about 10 ml to about 100 ml and in the third set of infusion containers at a concentration of 0.2 mg/ml and at a volume ranging from about 10 ml to about 100 ml.

In one preferred embodiment, wherein the drug is Irinotecan hydrochloride, the currently approved product of Irinotecan hydrochloride (Camptosar®) is indicated for the treatment of metastatic colorectal cancer with following two treatment regimens, (colorectal combination regimens and colorectal single-agent regimens) wherein the target dose of irinotecan to be delivered is based on body surface area (BSA).

a) Colorectal Combination Regimens:
　125 mg/m$^2$ intravenous (i.v.) infusion over 90 minutes on Days 1, 8, 15, 22 in 6-week cycles with 5-flourouracil and leucovorin
　180 mg/m$^2$ i.v. infusion over 90 minutes on Days 1, 15, 29 in 6-week cycles with 5-flourouracil and leucovorin b) Colorectal Single-Agent Regimens
   125 mg/m² i.v. infusion over 90 minutes on Days 1, 8, 15, 22 followed by a 2-week rest
   350 mg/m² i.v. infusion over 90 minutes once every 3 weeks Essentially, the approved dose is either 125 mg/m² or 180 mg/m² or 350 mg/m² based on the body surface area for different dosage regimens. For a patient having a body surface area of 1.8 m², the single daily target dose that is needed can be calculated which comes to be 225 mg or 324 mg or 630 mg, respectively. This dose can be delivered within ±5% variance by the method of the present invention by selecting first set of infusion containers and if required selecting one or more infusion containers from the second and third sets of infusion containers of the present invention. For instance, to deliver a 225 mg dose, one can select a first set of perfusion container that have 150 ml of aqueous solution of irinotecan hydrochloride at a concentration of 1.5 mg/ml. For delivering 324 mg, one can select a first set of perfusion container that have 210 ml of aqueous solution of irinotecan hydrochloride at a concentration of 1.5 mg/ml and additionally a second set of perfusion container that have 50 ml of aqueous solution of irinotecan hydrochloride at a concentration of 0.2 mg/ml. The dose delivered by these containers is 325 mg, i.e. 0.3% more than the calculated desired dose of 324 mg and is within ±5% variance limit.

In this illustrative embodiment, wherein the drug is Irinotecan hydrochloride, suitable instructions may be provided according to the method or system of the present invention to calculate the dose to be administered based on one of patient's parameters, such as patient's body surface area and for selecting one or more perfusion container(s) from the first set and if required one or more top-up perfusion container(s) from the second or third set and for directly administering the drug from the selected perfusion containers such that the delivered dose is equal to or within ±5% of the calculated dose. Such instructions for example are illustrated below in Tables a, b and c.

According to one embodiment of the method or system of the present invention, there is provided calculation of dose and instructions for selecting one or more perfusion containers for administering drug, irinotecan hydrochloride at a dose of 125 mg/m2, in accordance with body surface area as the patient parameter in table (a) below:

TABLE (a)

| BSA (m²) | Total Target Dose to be delivered (mg) D | First set of Perfusion container Drug concentration- 1.5 mg/ml: Volume delivered from first perfusion container (ml) | Dose delivered from first perfusion container (a) (mg) | Top-up perfusion containers- Second set Drug concentration- 0.4 mg/ml: Volume delivered from second top up perfusion container (ml) | Dose delivered from top-up container (b) (mg) | Top-up perfusion containers- Third set Drug concentration- 0.2 mg/ml: Volume delivered from third top up perfusion container (ml) | Dose delivered from top-up container (c) (mg) | Total dose delivered (mg) (a + b + c) | % Variation** from delivered dose Vs calculated dose |
|---|---|---|---|---|---|---|---|---|---|
| 1.3 | 162.5 | 90  | 135 | 50 ml | 20 mg | 50 ml | 10 mg | 165 | 1.5 |
| 1.4 | 175   | 120 | 180 | 0     | 0     | 0     | 0     | 180 | 2.86 |
| 1.5 | 187.5 | 120 | 180 | 0     | 0     | 50 ml | 10 mg | 190 | 1.3 |
| 1.6 | 200   | 120 | 180 | 50 ml | 20 mg | 0     | 0     | 200 | 0 |
| 1.7 | 212.5 | 120 | 180 | 50 ml | 20 mg | 50 ml | 10 mg | 210 | −1.2 |
| 1.8 | 225   | 150 | 225 | 0     | 0     | 0     | 0     | 225 | 0 |
| 1.9 | 237.5 | 150 | 225 | 0     | 0     | 50 ml | 10 mg | 235 | −1.1 |
| 2.0 | 250   | 150 | 225 | 50 ml | 20 mg | 0     | 0     | 245 | −2.0 |
| 2.1 | 262.5 | 180 | 270 | 0     | 0     | 0     | 0     | 270 | 2.86 |
| 2.2 | 275   | 180 | 270 | 0     | 0     | 0     | 0     | 270 | −1.8 |
| 2.3 | 287.5 | 180 | 270 | 50 ml | 20 mg | 0     | 0     | 290 | 0.9 |
| 2.4 | 300.0 | 180 | 270 | 50 ml | 20 mg | 50 ml | 10 mg | 300 | 0 |

**% Variation from delivered dose Vs calculated dose = [((a + b + c) − D]/D × 100

One or more perfusion containers may be suitably selected from first, second and third set of perfusion containers to deliver the calculated target dose within ±5% of variation.

According to another embodiment of the method or system of the present invention, there is provided calculation of dose and instructions for selecting one or more perfusion containers for administering drug, irinotecan hydrochloride at a dose of 180 mg/m2, in accordance with body surface area as the patient parameter in table (b) below:

TABLE (b)

| BSA (m²) | Total Target Dose to be delivered (mg) D | First set of Perfusion container Drug concentration- 1.5 mg/ml: Volume delivered from first perfusion container (ml) | Dose delivered from first perfusion container (a) (mg) | Top-up perfusion containers- Second set Drug concentration- 0.4 mg/ml: Volume delivered from second top up perfusion container (ml) | Dose delivered from second top-up container (b) (mg) | Top-up perfusion containers- Third set Drug concentration- 0.2 mg/ml: Volume delivered from third top up perfusion container (ml) | Dose delivered from third top-up container (c) (mg) | Total dose delivered (a + b + c) | % Variation** from delivered dose Vs calculated dose |
|---|---|---|---|---|---|---|---|---|---|
| 1.3 | 234 mg | 150 ml | 225 mg | 0 | 0 | 50 ml | 10 mg | 235 mg | 0.4% |
| 1.4 | 252 mg | 150 ml | 225 mg | 50 ml | 20 mg | 50 ml | 10 mg | 255 mg | 1.2% |
| 1.5 | 270 mg | 180 ml | 270 mg | 0 | 0 | 0 | 0 | 270 mg | 0% |
| 1.6 | 288 mg | 180 ml | 270 mg | 50 ml | 20 mg | 0 | 0 | 290 mg | 0.7% |
| 1.7 | 306 mg | 210 ml | 315 mg | 0 | 0 | 0 | 0 | 315 mg | 2.9% |
| 1.8 | 324 mg | 210 ml | 315 mg | 0 | 0 | 50 ml | 10 mg | 325 mg | 0.3% |
| 1.9 | 342 mg | 210 ml | 315 mg | 50 ml | 20 mg | 50 ml | 10 mg | 345 mg | 0.88% |
| 2.0 | 360 mg | 240 ml | 360 mg | 0 | 0 | 0 | 0 | 360 mg | 0% |
| 2.1 | 378 mg | 240 ml | 360 mg | 50 ml | 20 mg | 0 | 0 | 380 mg | 0.5% |
| 2.2 | 396 mg | 270 ml | 405 mg | 0 | 0 | 0 | 0 | 405 mg | 2.27% |
| 2.3 | 414 mg | 270 ml | 405 mg | 0 | 0 | 50 ml | 10 mg | 415 mg | 0.2% |
| 2.4 | 432 mg | 270 ml | 405 mg | 50 ml | 20 mg | 50 ml | 10 mg | 435 mg | 0.7% |

**% Variation from delivered dose Vs calculated dose = [((a + b + c) − D]/D × 100

One or more perfusion containers may be suitably selected from first, second and third set of perfusion containers to deliver the calculated target dose within ±5% of variation.

According to another embodiment of the method or system of the present invention, there is provided calculation of dose and instructions for selecting one or more perfusion containers for administering drug, irinotecan hydrochloride at a dose of 350 mg/m2, in accordance with body surface area as the patient parameter in table (c) below:

TABLE (c)

| BSA (m²) | Total Target Dose to be delivered (mg) D | First set of Perfusion container Drug concentration- 1.5 mg/ml: Volume delivered from first perfusion container (ml) | Dose delivered from first perfusion container (a) (mg) | Top-up perfusion containers- Second set Drug concentration- 0.4 mg/ml: Volume delivered from second top up perfusion container (ml) | Dose delivered from second top-up container (b) (mg) | Top-up perfusion containers- Third set Drug concentration- 0.2 mg/ml: Volume delivered from third top up perfusion container (ml) | Dose delivered from third top-up container (c) (mg) | Total dose delivered (a + b + c) (mg) | % Variation** from delivered dose Vs calculated dose |
|---|---|---|---|---|---|---|---|---|---|
| 1.3 | 455 mg | 270 ml | 405 mg | 100 ml (50 × 2) | 40 mg | 0 | 0 | 445 mg | −2.2% |
| 1.4 | 490 mg | 240 ml | 360 mg | 0 | 0 | 0 | 0 | 495 mg | 1.0% |
|  |  | 90 ml | 135 mg | 0 | 0 | 0 | 0 |  |  |
| 1.5 | 525 mg | 240 ml | 360 mg | 0 | 0 | 0 | 0 | 515 mg | −1.9% |
|  |  | 90 ml | 135 mg | 50 ml | 20 mg | 0 | 0 |  |  |
| 1.6 | 560 mg | 270 ml | 405 mg | 50 ml | 20 mg | 0 | 0 | 560 mg | 0% |
|  |  | 90 ml | 135 mg | 0 | 0 | 0 | 0 |  |  |
| 1.7 | 595 mg | 270 ml | 405 mg | 0 | 0 | 0 | 0 | 585 mg | 1.7 |
|  |  | 120 ml | 180 mg | 0 | 0 | 0 | 0 |  |  |
| 1.8 | 630 mg | 270 ml | 405 mg | 0 | 0 | 0 | 0 | 630 mg | 0% |
|  |  | 150 ml | 225 mg | 0 | 0 | 0 | 0 |  |  |

TABLE (c)-continued

| BSA (m²) | Total Target Dose to be delivered (mg) D | First set of Perfusion container Drug concentration- 1.5 mg/ml: Volume delivered from first perfusion container (ml) | Dose delivered from first perfusion container (a) (mg) | Top-up perfusion containers- Second set Drug concentration- 0.4 mg/ml: Volume delivered from second top up perfusion container (ml) | Dose delivered from second top-up container (b) (mg) | Top-up perfusion containers- Third set Drug concentration- 0.2 mg/ml: Volume delivered from third top up perfusion container (ml) | Dose delivered from top-up container (c) (mg) | Total dose delivered (a + b + c) (mg) | % Variation** from delivered dose Vs calculated dose |
|---|---|---|---|---|---|---|---|---|---|
| 1.9 | 665 mg | 270 ml | 405 mg | 0 | 0 | 0 | 0 | 675 mg | 1.5% |
|  |  | 180 ml | 225 mg | 0 | 0 | 0 | 0 |  |  |
| 2.0 | 700 mg | 270 ml | 405 mg | 50 ml | 20 mg | 0 | 0 | 695 mg | −0.7% |
|  |  | 180 ml | 225 mg | 0 | 0 | 0 | 0 |  |  |
| 2.1 | 735 mg | 270 ml | 405 mg | 50 ml | 20 mg | 0 | 0 | 740 mg | 0.7% |
|  |  | 210 ml | 270 mg | 0 | 0 | 0 | 0 |  |  |
| 2.2 | 770 mg | 270 ml | 405 mg | 0 | 0 | 0 | 0 | 765 mg | −0.65% |
|  |  | 240 ml | 360 mg | 0 | 0 | 0 | 0 |  |  |
| 2.3 | 805 mg | 270 ml | 405 mg | 0 | 0 | 0 | 0 | 810 mg | 0.62% |
|  |  | 270 ml | 405 mg | 0 | 0 | 0 | 0 |  |  |
| 2.4 | 840 mg | 270 ml | 405 mg | 50 ml | 20 mg | 0 | 0 | 830 mg | −1.2% |
|  |  | 270 ml | 405 mg | 0 | 0 | 0 | 0 |  |  |

** % Variation from delivered dose Vs calculated dose = [((a + b + c) − D]/D × 100

One or more perfusion containers may be suitably selected from first, second and third set of perfusion containers to deliver the calculated target dose within ±5% of variation.

The method and system of the present invention is particularly advantageous as it avoids the complex and error prone delivery of intravenous infusions that use concentrated solutions which require prior dilution before intravenous administration. For example, a comparison is made between the method of delivery of a specific dose of irinotecan using currently marketed concentrated product Camptosar® as against the system/method of the present invention. For illustrative purposes, in order to deliver a total dose of, 225 mg, Camptosar® being available at a concentration of 20 mg/mL in three sizes i.e 2 ml, 5 ml and 15 mL; following are the alternatives that can be followed.

- 2 ml vial (each vial contains 40 mg irinotecan hydrochloride)—Solutions from 5 vials and 1.25 ml from the 6ᵗʰ vial to be transferred to another container followed by dilution to 150 ml using a diluent such as dextrose solution. (the remaining 0.75 ml solution from 6ᵗʰ vial to be discarded)
- 5 ml vial (each vial contains 100 mg irinotecan hydrochloride)—Solutions from 2 vials and 1.25 ml from the 3ʳᵈ vial to be transferred to another container followed by diluted to 150 ml (remaining 3.75 ml solution from 3ʳᵈ vial to be discarded)
- 15 ml (each vial contains 300 mg irinotecan hydrochloride)—11.25 ml solution to be withdrawn from a 15 ml vial and further diluted q.s to 150 ml. (remaining 3.75 ml solution to be discarded).

The steps of dilution and administering a dose using Camptosar®, is complex, requires manipulation (dilution) and is prone to errors and also involve wastage of drug solution. In contrast, the method of the present invention provides for convenient delivery of the desired dose avoiding the aforesaid disadvantages. Thus, it is apparent that the method/system of the present invention conveniently provides different sets of perfusion containers containing ready-to-infuse, stable, sterile aqueous solution of the irinotecan hydrochloride and instructions for selecting the appropriate concentration using combination of the two or more perfusion container from either first and/or second or third set of perfusion containers so that accurate dose is delivered. For instance, to deliver a total dose of 225 mg, the method of the present invention provides a first set of perfusion bag having 150 ml of 1.5 mg/ml irinotecan hydrochloride and instructions for selecting the same.

The aqueous solution of drug in containers of the first set and containers of the second and third sets in one preferred embodiment, is similar in excipients except their concentrations. The pharmaceutically acceptable excipients or adjuvants that may be used in formulating the ready-to-infuse, stable, sterile, aqueous perfusion solution of drug include, but are not limited to pH adjusting and/or buffering agents, tonicity adjusting agents, chelating agents, solvents etc. In one embodiment, the aqueous perfusion solution of drug is preservative free.

Suitably, a pH adjusting and/or buffering agents is used to adjust the pH of the aqueous solution to a suitable range at which the drug solution is stable. The pH of the solution may be adjusted in the desired range by use of a pH adjusting agents and or a buffering agent known in the pharmaceutical art. The pH adjusting agents and/or buffering agents that may be used in the present invention may be selected from, but not limited to, tromethamine, lactic acid or its salts, acetic acid or its salts, boric acid or its salt, phosphoric acid or its salt, citric acid or its salt, tartaric acid or its salt, hydrochloric acid, sodium hydroxide, potassium hydroxide, sodium carbonate, sodium hydrogen carbonate, and the like and mixtures thereof.

In one preferred embodiment, the aqueous perfusion solution of irinotecan or its salts such as irinotecan hydrochloride is adjusted to a pH in the range of about 3.0 to about 4.5, preferably, about 3.5 to 4.25. In one specific embodiment, the pH of the solution is adjusted to about 3.5.

Suitably, the aqueous perfusion solution of drug filled in the perfusion containers, may contain an osmolality or tonicity adjusting agents in an amount sufficient to make the solution isoosmolar to blood plasma, i.e. to provide an osmolality in the range of about 250-375 mOsm/kg, preferably 280-320 mOsm/kg. The tonicity adjusting agents that may be used in the present invention are selected from, but not limited to, dextrose, sucrose, sodium chloride, potassium chloride, calcium chloride, mannitol, glycerol, sorbitol, propylene glycol, and the like, and mixtures thereof. Preferably, the tonicity adjusting agent is dextrose.

Suitably, the perfusion containers according to the method of the present invention may be a perfusion bag, infusion bag, flexible pouch or soft bag. The container is made up of a suitable material such as plastic or other polymeric material. The container may include one or more layers of such materials, thus the container may be single or multiple layered. In preferred embodiments, the material of construction of the perfusion containers is such that it can withstand terminal sterilization, such as autoclaving. Suitably, the material of construction of the perfusion containers may be selected from, but not limited to, polyolefin polymers, polyethylene, polypropylene; cyclo olefin polymers, cyclo olefin copolymers, polypropylene based polyolefin polymers; polycarbonates; modified polyolefin-polyethylene polymers or styrene-polyolefin based polymers and block co-polymers thereof. Suitably, the container may have material that contains borate or boron. Preferably, according to one embodiment, the container does not contain polyvinylchloride. The containers are easy to handle and transport. The perfusion containers are not impermeable in nature and possess some permeation characteristics and the aqueous solution of drug remains in contact with these materials of the container throughout the shelf life of the dosage form.

In one specific preferred embodiment, the perfusion containers are made up of an outer layer of polyamide 11, a middle tie of modified polyolefin and an inner layer of linear low density polyethylene. These containers have a water vapour transmission rate of 2 g ($m^2$.day) when measured at (40° C./90% relative humidity); oxygen transmission rate of 900 ml/($m^2$0.24 hour.atm) when measured at (23° C./0% relative humidity) and carbon dioxide transmission rate of 600 ml/($m^2$0.24 hour.atm) when measured at 23° C./0% relative humidity. Such containers are available commercially and are manufactured by Hosokawa as Polyelite®AE-1. In another preferred embodiment the perfusion containers may be made up of a material comprising a polymer of cyclic olefin such as cycloolefin homopolymer or cycloolefin copolymer or mixture thereof. Specifically, in a particular embodiment, the container comprises an inner layer made up of a cycloolefin polymer, a middle layer made up of linear low density polyethylene polymer and an outer layer made up of low density polyethylene polymer. Such containers are available commercially and are manufactured by Hosokawa as Polyelite®EHC film bag. In another embodiment, the perfusion containers may be made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially and are manufactured by Technoflex These type of containers have a water vapour transmission rate of 0.62 g ($m^2$.day) when measured at 23° C./60% relative humidity; oxygen permeability of 1110 ml/($m^2$0.24 hour.atm) when measured at 23° C./40% relative humidity and carbon dioxide transmission rate of 5149 ml/($m^2$0.24 hour.atm). Alternatively, the perfusion containers may be made up of multilayer polyolefin film (M312 and M312A) with a multilayered polyolefin tubing (M916 and M916A). Such containers are available under the brand names of Sippex.

Figure 1:
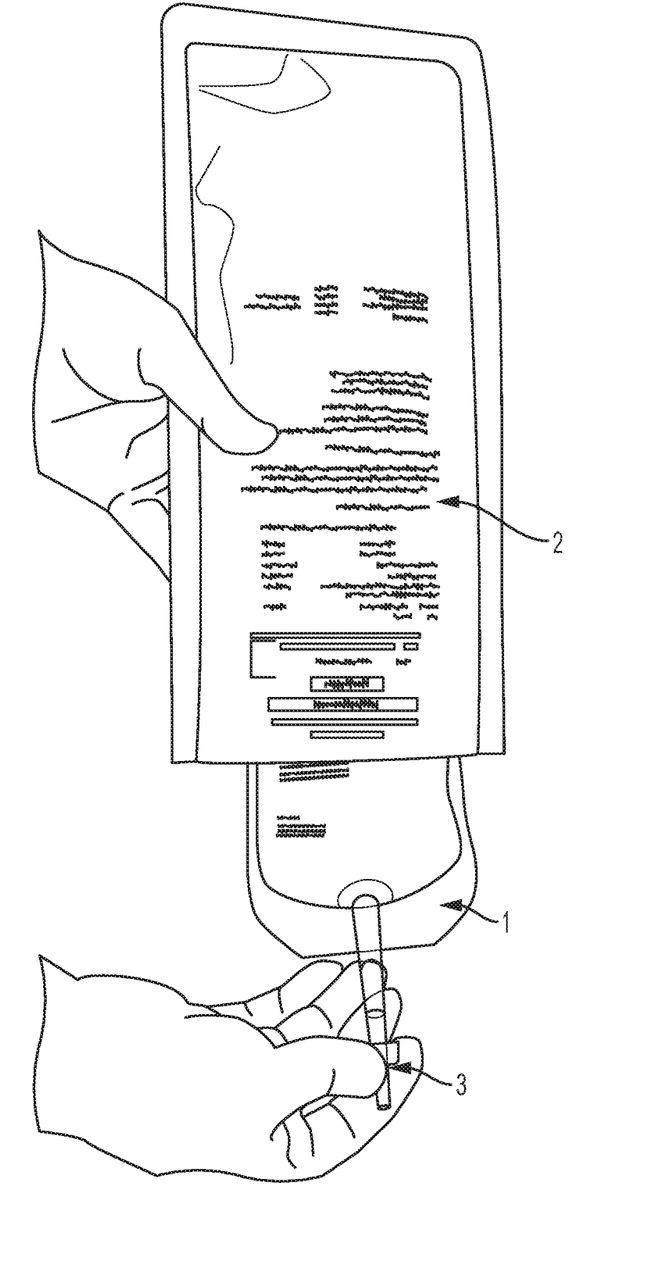
FIG. 1 represents the configuration of the perfusion dosage form, wherein 1 is perfusion bag filled with ready-to-infuse, stable, sterile aqueous solution of a drug, 2 is the secondary package—an overwrap aluminum pouch and 3 is a single exit port for delivering of the solution by intravenous route.

In one embodiment, the perfusion containers have a single outlet for withdrawal of the aqueous solution from the container while being administered intravenously. Suitably all of the containers have such a single outlet. This design avoids any manipulation, such as volume adjustment (addition or removal of aqueous solution) prior to intravenous infusion. According to one preferred embodiment, the single outlet is a single infusion port or connector, which in one embodiment may have three assembled parts including a central stopper made up of chlorobutyl rubber (latex free); an upper breakable part and a bottom part, both made up of polycarbonate. Such ports are available under the brand names of Minitulipe®. In one specific embodiment, the stopper is made up of Minitulipe M95A spike port with chlorobutyl (latex free) 6321 GS joint Sippex 323. The perfusion container with single outlet port is represented by FIG. 1. In one embodiment, the infusion port allows for insertion of an infusion set, cannula/needle prior to administration such that it allows a tight connection with the infusion line and allows for single outward flow of the aqueous solution. In one embodiment, the perfusion container and the delivery port connecting to the infusion needle forms a system whereby during intravenous administration of the solution to the patient, the vacuum created by outgress of solution is accommodated by the elasticity or flexibility of the perfusion container instead of ingress of external non-sterile air, which advantageously maintains and ensures sterility of the solution until it reaches the patient.

In one embodiment, the perfusion container includes a thermally resealable portion that is fusible in response to thermal energy, and a container body having a sealed empty chamber in fluid communication with the resealable portion for receiving therein the aqueous solution of the present invention. The method of filling the container includes penetrating the resealable portion with an injection member and introducing the aqueous solution of the present invention into the chamber, withdrawing the injection member while engaging the base of the body to substantially prevent axial movement of the body, and applying thermal energy to the resealable portion to thermally fuse the penetrated region thereof. Such systems are elaborated in United States patent number U.S. Pat. No. 7,992,597, which is incorporated herein by reference.

In another embodiment, the perfusion container may include a chamber for receiving aqueous solution of the present invention and a thermoplastic portion in fluid communication with the chamber. The thermoplastic portion defines a penetrable region that is penetrable by a filling member and is heat resealable to hermetically seal an aperture therein by applying laser radiation at a predetermined wavelength and power and in a predetermined time period. Such systems are elaborated in United States patent number U.S. Pat. No. 7,490,639, which is incorporated herein by reference.

In yet another embodiment, the perfusion container include a sealed chamber; a first penetrable septum in fluid communication with the chamber that is formed of an elastic material and is penetrable by a first injection member to fill the first chamber with the aqueous solution of the present invention therethrough; and a second penetrable septum movable between first and second positions. In the first position, at least a portion of the second septum is spaced away from the first septum to allow the injection member to penetrate the first septum and aseptically or sterile fill the chamber with the aqueous solution of the present invention therethrough. In the second position, the portion of the second septum overlies and seals a resulting injection aperture in the first septum after withdrawal of the first injection member therefrom, and is penetrable by a second injection member to penetrate the first and second septums and withdraw the filled aqueous solution of the present invention from the chamber and through the second injection member. Such systems are elaborated in United States patent application number US20130333796, which is incorporated herein by reference.

The perfusion containers which do not have any resealable portions may also be used according to the method or system of the present invention. The perfusion containers filled with aqueous solution of drug are sterilized by way of terminal sterilization. Preferably, the terminal sterilization is done by autoclaving of the filled perfusion containers. Preferably, the terminal sterilization techniques used in the present invention include use of counter pressure sterilizers such as 'Super heated water sterilizer' and 'steam air mixture sterilizers'. According to one preferred embodiment, the terminal sterilization is carried out via autoclaving in a super heated water spray sterilizer at following process parameters—Minimum Sterilization Temperature-121.0° C.; Maximum Sterilization Temperature—122.0° C.; Control Temperature—121.5° C.; Exposure Time—15.0 minutes and Sterilization Pressure—3.50 bar.

In one embodiment, the perfusion containers that have been sterilized as described above, are packaged in a secondary packaging that surrounds the perfusion container. The secondary packaging may comprise a second container such as a pouch or overwrap or carton. The secondary packaging may comprise a suitable pouch, such as an aluminium pouch covering the perfusion container of the first component. It may further comprise an oxygen scavenger in between the perfusion container and overwrap or pouch. In one preferred embodiment, the secondary packaging comprises both an aluminium pouch and an oxygen scavenger. The secondary packaging may further comprise an outer black polyethylene bag and a fiberboard drum. Silica gel bags may optionally be placed between the aluminum pouch and the black polyethylene bags. In one embodiment, either the perfusion container of the first component or the secondary packaging, is designed to protect the solution of drug from light. Suitably, in one embodiment, the material of the perfusion container is such that it provides light protection. The container may be amber colored or opaque to provide protection from light. In another embodiment, the material of construction of the perfusion container is such that the containers are transparent which makes it possible to carry out visual inspection of the drug solution prior to and during administration of the drug solution, which ensures safety. In this embodiment, the secondary packaging-pouch or overwrap or carton is made up of a suitable light protective material such as for example aluminum. In one embodiment, the secondary packaging/aluminium pouch incorporates a transparent window for visual inspection of the aqueous drug solution. In one embodiment, the space between the perfusion container and secondary packaging is occupied with an inert gas such as nitrogen or argon.

The present invention in one embodiment also provides a perfusion system comprising a first set of perfusion containers comprising, consisting essentially or containing a ready-to-infuse, stable, sterile, aqueous perfusion solution of the drug at a first higher concentration, and a second set of top-up perfusion containers comprising, consisting essentially or containing a ready-to-infuse, stable, sterile, aqueous perfusion solution of the drug at a second concentration and optionally a third set of top-up perfusion containers comprising, consisting essentially or containing a ready-to-infuse, stable, sterile, aqueous perfusion solution of the drug at a third concentration, the first concentration of drug being higher than the second and third concentrations, the first to the third sets of perfusion containers ranging in volume from a higher volume to a lower volume, wherein the set of perfusion containers alone or in combination provide for direct intravenous administration of desired dose of the drug to a patient in need thereof, such that the delivered dose is equal to or within ±5% of the desired dose calculated based on one of patient's parameters.

Particularly, the present invention also relates to a perfusion system comprising:

a first set of perfusion containers comprising a ready-to-infuse, stable, sterile, aqueous perfusion solution of a drug at a first higher concentration, and a second set of top-up perfusion containers comprising a ready-to-infuse, stable, sterile, aqueous perfusion solution of the drug at a second concentration and optionally a third set of top-up perfusion containers comprising a ready-to-infuse, stable, sterile, aqueous perfusion solution of the drug at a third concentration, the first concentration of drug being higher than the second and third concentrations, the first to the third sets of perfusion containers ranging in volume from a higher volume to a lower volume, instructions for selecting one or more perfusion container(s) from the first set and if required one or more top-up perfusion container(s) from the second or third set and for directly administering the drug from the selected perfusion containers such that the delivered dose is equal to or within ±5% of a dose calculated according to at least one patient parameter, wherein the set of perfusion containers alone or in combination provides for direct intravenous administration of a desired dose of the drug to a patient in need thereof, such that the delivered dose is equal to or within ±5% of the calculated dose.

The present invention in one embodiment also provides a first set of perfusion containers containing a ready-to-infuse, stable, sterile, aqueous perfusion solution of irinotecan or its pharmaceutically acceptable salt at a first higher concentration ranging from 1.0 mg/ml to 3.0 mg/ml, and a second set of top-up perfusion containers containing a ready-to-infuse, stable, sterile, aqueous perfusion solution of irinotecan or its pharmaceutically acceptable salt at a second concentration ranging from 0.1 mg/ml to 0.6 mg/ml, and optionally a third set of top-up perfusion containers having a ready-to-infuse, stable, sterile, aqueous perfusion solution of irinotecan or its pharmaceutically acceptable salt at a third concentration ranging from 0.1 mg/ml to 0.6 mg/ml, the set of perfusion containers ranging in volume from a 10 ml to 500 ml, wherein the set of perfusion containers alone or in combination provide for direct intravenous administration of desired dose of the drug to a patient in need thereof, such that the delivered dose is equal to or within ±5% of the desired dose calculated based on one of patient's parameters. Generally the volume of a container from the first set of containers is greater than the volume of a container from the second set of containers, and the volume of a container from the third set of containers is generally less than the volume of a container from the second set of containers. In one preferred embodiment, wherein the drug is irinotecan hydrochloride, the perfusion containers are multilayered and are flexible. The outermost layer which is not in contact with the aqueous solution is made up of polyamide, a middle layer made up of modified polyolefin and the innermost layer which is in contact with the aqueous solution of irinotecan is made up of linear low density polyethylene. The perfusion containers are same for all the set of containers. The containers are overwrapped with a light protective material having oxygen scavenger. The overwrapped material may be an aluminum pouch. The ready-to-infuse aqueous solution comprise an osmotic agent in an amount sufficient to make the solution isoosmolar and a pH adjusting agent or a buffer to adjust and maintain the pH in the range of 3.0 to 4.5. The filled perfusion containers are sterilized by terminal sterilization, such as autoclaving i.e. wet heat sterilization or steam sterilization at 121° C. for 15 minutes at 3.5 bar pressure. These sterilized filled perfusion container are then packed in secondary packaging which is designed to protect the solution of drug from light. More preferably in this embodiment, the osmotic agent is selected from dextrose, glucose, sorbitol or mixtures thereof and the pH adjusting agent is selected from lactic acid, hydrochloride acid, sodium hydroxide or mixtures thereof.

Suitably, according to the present invention, the perfusion dosage form or the ready-to-infuse aqueous solution of drug filled in the perfusion container is physically as well as chemically stable as demonstrated by compliance to acceptable specification, when the dosage form is stored at room temperature (20-25° C. and 40% relative humidity) for at least twelve months, preferably eighteen months, more preferably 24 months or longer. The dosage form also show compliance to acceptable specification when stored at accelerated stability testing condition of 40° C./25% relative humidity for 6 months, which correlate with stability for 2 years of shelf life. Various parameters such as the drug content (assay) and content of related substances, i.e. known and unknown impurities remains within specified limits such as those specified according to ICH guidelines or pharmacopeias.

In one preferred embodiment wherein the drug is irinotecan, the ready-to-infuse aqueous solution of irinotecan remains physically stable, with solution being clear, free from visible particulate matter, no precipitation or crystallization or color change upon storage and the value of percentage transmittance of the solution remaining greater than 90%, preferably greater than 95% upon storage at room temperature for the shelf life period of 18-24 months. Further, the solution of irinotecan remains chemically stable when stored at room temperature (about 25° C.) for at least 12 months and at 40° C./25% relative humidity for 6 months, wherein various parameters such as the drug content (assay of irinotecan) and content of related substances, i.e. known and unknown impurities remains within specified limits upon storage. Suitably, the value of assay of irinotecan remains within the specified limit of 90%-110% by weight of the label claim; the highest unknown impurity remains within the specified limit of not more than 0.2%; the known impurities or related substances remains within the specified limit of not more than 0.2% and the total impurities remain within the specified limit of not more than 1.0%. The sealed perfusion bags comprising aqueous solution of Irinotecan hydrochloride remains stable for the shelf life when stored at 20° C. –25° C. (68-77° F.) and that allows for excursions between 15° and 30° C. (59° and 86° F.).

Hereinafter, the invention will be more specifically described by way of Examples. The examples are not intended to limit the scope of the invention and are merely used as illustrations.

EXAMPLE 1

TABLE 1

Set of Perfusion containers having Irinotecan hydrochloride drug:

| | Different sets of perfusion containers | | | | | | |
|---|---|---|---|---|---|---|---|
| | 90 mL | 120 mL | 150 mL | 180 mL | 210 mL | 240 mL | 270 mL |
| | Amount in mg | | | | | | |
| Ingredients | | | | | | | |
| Irinotecan hydrochloride trihydrate | 135 | 180 | 225 | 270 | 315 | 360 | 405 |
| Sorbitol | 303.75 | 405 | 506.25 | 607.5 | 708.75 | 810 | 911.25 |
| Lactic acid | 6.075 | 8.100 | 10.125 | 12.150 | 14.175 | 16.2 | 18.225 |
| Dextrose (anhydrous) | 4162.5 | 5550 | 6937.5 | 8325 | 9712.5 | 11100.0 | 12487.5 |
| HCl | For pH adjustment in the range of 3-5 | | | | | | |
| NaOH | For pH adjustment in the range of 3-5 | | | | | | |
| | Concentration (mg/ml) | | | | | | |
| Irinotecan hydrochloride | 1.5 | | | | | | |
| Sorbitol | 3.375 | | | | | | |
| Lactic acid | 0.0675 | | | | | | |
| Dextrose | 46.25 | | | | | | |

The composition of ready-to-infuse aqueous solutions of irinotecan and method of preparation is given below:

TABLE 2

Composition of ready-to-infuse aqueous solutions of irinotecan

| Ingredient | Quantity mg/mL |
|---|---|
| Irinotecan hydrochloride, USP | 0.2 mg-2.0 mg |
| Dextrose, USP (anhydrous) | 40-50 mg |
| Sorbitol, NF | 2-5 mg |
| Lactic acid, USP | 0.01-0.1 mg |
| Sodium hydroxide, NF and Hydrochloric acid, NF | q.s. to adjust pH in the range of 3-5 |
| Water for injection, USP | q.s. to 1 mL | q.s. = quantity sufficient

Water for injection was purged with nitrogen. Dextrose was added and dissolved with stirring, followed by addition and dissolution of sorbitol. Lactic acid was then added and dissolved with stirring. Irinotecan hydrochloride was then added slowly into the above bulk solution with continuous stifling until complete dissolution and pH was checked. pH was then adjusted to 3 to 5 with 10% w/v hydrochloric acid or sodium hydroxide solution. The solution was then filtered through membrane filter cartridge (0.2μ×10 in). The filtered bulk solution was filled in a perfusion bag and the bag was then stoppered. The stoppered perfusion container was then terminally sterilized via autoclaving in a super heated water spray sterilizer. The perfusion bag was then over wrapped in an aluminum pouch and an oxygen scavenger was placed in between the container and aluminum pouch.

The process parameters at which terminal sterilization was carried out are given below in Table 3

TABLE 3

Autoclaving process parameters

| Process parameters | Value/Level |
|---|---|
| 1. Minimum Sterilization Temperature | 121.0° C. |
| 2. Maximum Sterilization Temperature | 122.0° C. |

TABLE 3-continued

Autoclaving process parameters

| Process parameters | Value/Level |
|---|---|
| 3. Control Temperature | 121.5° C. |
| 4. Exposure Time | 15.0 minute |
| 5. Sterilization Pressure | 3.50 bar |

Different batches of perfusion dosage forms prepared according to Example 1 were charged for stability testing at varying storage conditions—i.e. long term stability testing at controlled room temperature 25° C./40% relative humidity as well as at accelerated stability testing condition at 40° C./25% relative humidity. The observations for various parameters for three different batches are tabulated in table 4-6.

TABLE 4

Chemical and physical stability results of one batch:

| Analytical Test | Initial | 25° C./40% RH Six months | 30° C./35% RH Six months | 40° C./25% RH Six months |
|---|---|---|---|---|
| Assay of Irinotecan | 101.44 | 100.76 | 100.42 | 101.20 |
| Related compound B* (Impurity A) | 0.121 | 0.132 | 0.134 | 0.147 |
| Highest unknown Impurity | 0.097 | 0.114 | 0.135 | 0.139 |
| Total Impurity | 0.724 | 0.638 | 0.634 | 0.653 |
| Osmolality (mOsm/Kg) | 292 | 295 | 293 | 296 |
| pH | 3.98 | 3.90 | 3.92 | 3.90 |
| % T at 650 nm | 99.879 | 100.000 | 100.000 | 100.000 |

% T = percentage transmittance:
RH = Relative Humidity
*Related compound B-(S)-4,11-Diethyl-4,9-dihydroxy-1H-pyrano[3',4':6,7]indolizino[1,2-b]quinoline-3,14 (4H, 12H)-dione.

TABLE 5

Chemical and physical stability results of second batch:

| Analytical Test | Initial | 25° C./40% RH Six months | 40° C./25% RH Six months |
|---|---|---|---|
| Assay of Irinotecan | 100.33 | 101.09 | 100.98 |
| Related compound B* (Impurity A) | 0.137 | 0.126 | 0.145 |
| Highest unknown Impurity | 0.106 | 0.118 | 0.138 |
| Total Impurity | 0.789 | 0.626 | 0.615 |
| Osmolality (mOsm/Kg) | 291 | 294 | 293 |
| pH | 4.16 | 3.83 | 3.93 |
| % T at 650 nm | 100.0 | 100.0 | 100.0 |

% T = percentage transmittance:
RH = Relative Humidity
*Related compound B-(S)-4,11-Diethyl-4,9-dihydroxy-1H-pyrano[3',4':6,7]indolizino[1,2-b]quinoline-3,14 (4H, 12H)-dione.

TABLE 6

| Analytical Test | Limits | Initial | 25° C./40% RH After 12 month | 40° C./25% RH After 6 month |
|---|---|---|---|---|
| Assay of Irinotecan | 90%-110% | 99.89 | 99.33 | 99.5 |
| Related compound B* (Impurity A) | NMT 0.2% | BQL | BQL | BQL |
| Highest unknown Impurity | NMT 0.2% | 0.096 | 0.096 | 0.107 |
| Total Impurity | NMT 1.0% | 0.192 | 0.196 | 0.253 |
| Osmolality (mOsm/Kg) | 250-350 | 289 | 287 | 297 |
| pH | 3-5 | 3.67 | 3.55 | 3.48 |
| % T | NLT 95% | 99.9 | 100 | 100 |

RH = Relative Humidity;
BQL—Below Quantifying limit;
NMT—Not more than;
% T = percentage transmittance
*Related compound B is (S)-4,11-Diethyl-4,9-dihydroxy-1H-pyrano[3',4':6,7]indolizino[1,2-b]quinoline-3,14(4H,12H)-dione;
NLT—Not less than It was observed that in all the batches, the assay of the drug remains within the specified limit upon storage. All impurities, highest unknown impurity, total impurities and related compounds remain within specified limits upon storage. The particulate matter remains within specification upon storage and the solution remains clear. The percentage transmission, which is an indicator of the clarity of the solution does not change, it remains about 100% indicating that the solution maintains proper clarity. There occurs no substantial change in the osmolality and pH of the solution upon storage. Thus, it can be concluded that the perfusion dosage form of the present invention maintains proper stability, physical and chemical, through out the shelf life.

The invention claimed is:

1. A perfusion dosage form comprising:
   a flexible perfusion container containing from 50 ml to 500 ml of a ready-to-infuse aqueous perfusion solution comprising irinotecan hydrochloride at a concentration in a range from 0.2 mg/ml to 2 mg/ml, tonicity adjusting agent, water for injection, and lactic acid, the solution having a pH in a range from 3.0 to 4.5, wherein the flexible perfusion container has a single outlet configured to provide a single outward flow of the solution, wherein the flexible perfusion container is terminally sterilized by autoclaving, and
   a secondary packaging designed to protect the solution from light, the secondary packaging surrounding said flexible perfusion container,
   wherein the solution has a total impurity of less 1.0%, a highest unknown impurity not more than 0.2%, and an impurity A not more than 0.2%, when the perfusion dosage form is stored at 25° C/40% R.H. for 12 months.

* * * * *